United States Patent [19]

Golec, Jr. et al.

[11] Patent Number: 4,535,177

[45] Date of Patent: Aug. 13, 1985

[54] N-SUBSTITUTED AMINO ACID DERIVATIVES

[75] Inventors: Frederick A. Golec, Jr., Ossining; Thomas Goetzen, Tuckahoe, both of N.Y.

[73] Assignee: USV Pharmaceutical Corp., Tarrytown, N.Y.

[21] Appl. No.: 551,448

[22] Filed: Nov. 14, 1983

[51] Int. Cl.$^3$ ............................................. C07C 101/20
[52] U.S. Cl. ...................................... 560/38; 548/497
[58] Field of Search ................... 560/35, 38, 39, 168, 560/42, 43, 16, 20, 21, 22, 34, 40, 41, 147, 153, 156, 169, 170, 171, 179; 564/271, 276, 278; 562/426, 443, 444, 445, 449, 450, 556, 564, 565, 568, 571, 574; 548/341, 342, 495, 497

[56] References Cited

U.S. PATENT DOCUMENTS

| | | | |
|---|---|---|---|
| 2,520,042 | 8/1950 | Lisk et al. | 560/35 |
| 3,778,463 | 12/1973 | Gronowitz et al. | 560/35 |
| 3,894,051 | 7/1975 | Suh | 564/276 |
| 4,350,704 | 9/1982 | Hoefle et al. | 424/258 |

OTHER PUBLICATIONS

Yamada et al., "Asymmetric Transamination from Amino Acids (I)", *Tetrahedron Letters*, 1976, (13), pp. 997-1000.

*Primary Examiner*—Natalie Trousof
*Assistant Examiner*—Bruce D. Gray

[57] ABSTRACT

Optical isomeric compounds having the general formula

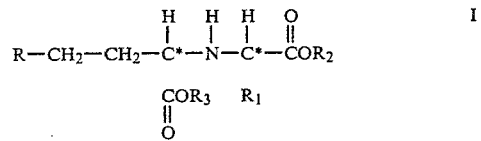

are prepared by: reacting by catalytic hydrogenation a compound of the formula

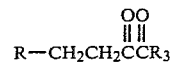

with a compound of the formula

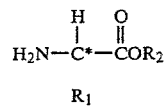

wherein R, $R_1$, $R_2$ and $R_3$ are as defined herein, to form a mixture of isomers in a ratio of L(S)L(S)>D(R)L(S); and recovering the (S,S) diastereomer by selectively precipitating an acid salt of the (S,S) ester from the solution.

16 Claims, No Drawings

N-SUBSTITUTED AMINO ACID DERIVATIVES

BACKGROUND OF THE INVENTION

This invention relates to new chemical compounds useful as intermediates for the preparation of compounds having valuable pharmaceutical properties. The invention particularly relates to a steroselective reductive alkylation process for the preparation of novel asymmetric N-substituted amino acid derivative intermediates useful in the preparation of Angiotensin Converting Enzyme Inhibitor (ACEI) compounds.

Syntheses with asymmetric induction have been known in the prior art. A synthesis with asymmetric induction is commonly defined as a process in which a chiral unit in an ensemble of substrate molecules induces, by a reaction with achiral units, resulting molecules in such a manner that the stereoisomeric products are produced in unequal amounts. Such an asymmetric synthesis may be of great economic value for excluding or reducing the amount of unwanted isomers when only one of the diastereomers is of use or interest.

The reactants used in an asymmetric synthesis can be at least one chiral component consisting of a chemical reagent, solvent, catalyst or an energy such as circularily polarized light. Alternatively, by selection of specific enantiomers as starting compounds, the preferred stereoisomer in predominant amount can be induced.

An object of the present invention is to provide asymmetric N-substituted amino acid derivatives in which the (S,S) diastereomeric compound predominates.

Another object of the present invention is to provide a process for synthesizing asymmetric N-substituted amino acid derivatives which process is simple utilizing readily available starting materials, economical, and which can be conveniently scaled up to industrial scale production.

DESCRIPTION OF THE INVENTION

The present invention relates to the (S,S) diastereoisomer of compounds of the formula

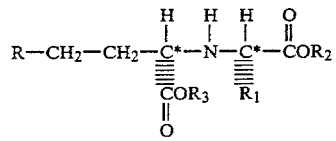

wherein

* denotes an asymmetrical center;

R is H, lower alkyl, aryl, aryl lower alkyl, aminomethyl phenyl lower alkyl, hydroxy phenyl lower alkyl, hydroxy lower alkyl, acetylamino lower alkyl, acylamino lower alkyl, dimethylamino lower alkyl, halo lower alkyl, imidazolyl lower alkyl, indolyl lower alkyl, mercapto lower alkyl, loweralkylthio lower alkyl, lower alkoxy, lower alkenoxy di (lower alkyl) amino lower alkoxy, hydroxy lower alkoxy, acylamino lower alkoxy, acyloxy lower alkoxy, aryloxy, aryloxy lower alkoxy, lower alkylamino or N-hydroxyamino;

$R_1$ is lower alkyl, aryl, aryl lower alkyl, aminoethyl phenyl lower alkyl, hydroxy phenyl lower alkyl, hydroxy lower alkyl, acetylamino lower alkyl, acylamino lower alkyl, dimethylamino lower alkyl, halo lower alkyl, imidazolyl lower alkyl, indolyl lower alkyl, mercapto lower alkyl, or lower alkylthio lower alkyl; and $R_2$ and $R_3$ are independently H, lower alkyl, di(lower alkyl) amino, cycloalkyl, polycycloalkyl, cycloalkyl lower alkyl or aryl lower alkyl.

The alkyl groups per se or when present as substituents are preferably lower alkyl containing from 1 to 6 carbon atoms and may be straight or branched. These groups include methyl, ethyl, propyl, iso-propyl, butyl, isobutyl, amyl, hexyl and the like.

In the case of R the alkyl groups may carry substituents such as hydroxy, lower alkoxy, thio, lower alkylamino, di(lower alkyl) amino, halogen and nitro.

The cycloalkyl groups may be mono or polycyclic and contain from 3 to 20 carbons. These groups include cyclopropyl, cyclopentyl, cyclohexyl, cycloheptyl, bornyl, nor-bornyl, indanyl and the like. In the case of R these groups may be partially unsaturated and carry substituents such as halogen, hydroxy, lower alkyl, lower alkoxy, di(lower alkyl) amino, thiol, lower alkylmercapto, nitro, and trifluoromethyl.

The aryl groups contain from 6 to 10 carbon atoms and include such groups as phenyl and—or—naphthyl and fused phenyl-cycloalkyl such as indanyl. In the case of R the aryl group may carry one or more substituents such as lower alkyl, lower alkenyl, lower alkynyl, hydroxy, lower alkoxy, lower alkylamino, di(lower alkyl) amino, thiol, lower alkylmercapto, hydroxy lower alkyl, thio lower alkyl, nitro, halogen, trifluoromethyl, methylene-dioxy or ureido.

The alkenyl and alkynyl groups when present as substituents preferably contain from 2 to 6 carbon atoms and may be straight or branched.

The halogen group may be fluorine, chlorine, bromine and iodine.

An intermediate of particular interest has the formula

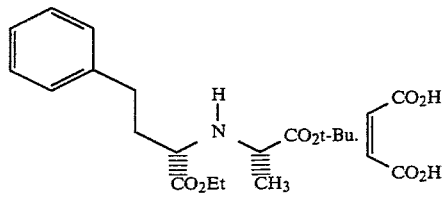

and is entitled N[(1S)-1-(ethoxycarbonyl)-3-phenylpropyl]-L-alanine, t-butyl ester. In accordance with recognized terminology, this configuration will be hereinafter referred to as (S,S).

A schematic representation for the synthesis of the compounds of the present invention is as follows:

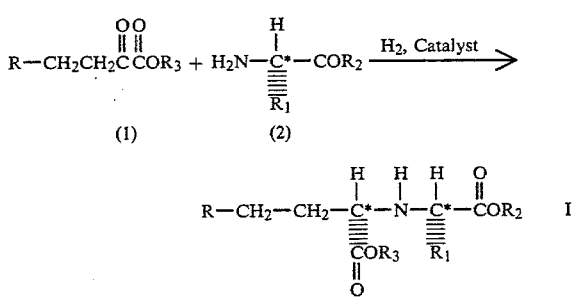

wherein R, $R_1$, $R_2$ and $R_3$ are as previously defined.

The starting materials denoted by (1), are commercially available pyruvate esters and may also be prepared by known synthetic procedures. (For example, L. M. Weinstock, R. B. Currie, A. V. Lovell, *Synth. Commun.* 11 (12), 943–946, 1981). We prefer to use the esters of naturally occurring amino acids, denoted by (2), which are available commercially or may be prepared by art recognized procedures. Examples of naturally occurring amino acids include: L-alanine, L-valine, L-leucine, L-isoleucine, L-phenylalanine, L-proline, L-serine, L-threonine, L-cysteine, L-cystine, L-methionine, L-tryptophan, L-tyrosine, L-asparagine, L-glutamine, L-aspartate, L-glutamate, L-lysine, L-arginine, L-histidine and the like.

In general, the synthesis of the compounds of the present invention is a stereoselective reductive alkylation synthesis with asymmetric induction and comprises the steps of:

a. dissolving a compound of the formula (2) in a reaction medium selected from the group consisting of an alcohol, such as methyl, ethyl, and propyl alcohol, a polar solvent, such as THF, dioxane, ethyl acetate and acetonitrile, or a mixture of water and a water miscible solvent, such as an alcohol;

b. adjusting the pH of the solution to 3–7;

c. adding with mixing a compound of formula (1) to the solution;

d. adding, based on weight of the reagent solution, about 0.1 to 20% w/w of a hydrogenation catalyst such as palladium, platinum, Raney nickel as is or with a catalyst support such as carbon, silica or zeolite to form a reaction mixture;

e. hydrogenating the reaction mixture on a hydrogenator such as a Parr hydrogenator at 0°–100° C., but preferably at about 20° C. to 30° C. and at atmospheric pressure, preferably higher, but not exceeding 25 atmospheres;

f. removing the catalyst, such as by filtering, decanting or centrifuging the hydrogenated mixture, and g. concentrating the filtrate, such as by evaporation in vacuo, or partitioning the filtrate between a water immiscible solvent such as toluene, ethyl acetate, chloroform and water to form an organic solvent extract containing the dissolved product.

The product of the reaction between compounds (1) and (2) is a mixture of diastereomers showing a predominance of the (S,S) diastereoisomer:

L(S)L(S) > D(R)L(S).

The reaction is therefore a stereoselective synthesis with asymmetric induction since an unequal mixture of diastereomeric products is obtained.

The desired (S,S) stereoisomer of the ester or acid of a compound of formula I is recovered by forming a salt of the mixed esters or acids with an acid, or a base in the case of acids, in a solvent medium and selectively precipitating the salt of the (S,S) isomer from the solution. We prefer to prepare maleic acid salts, although other pharmaceutically acceptable salts as defined in *J. Pharma. Sci.* 66 (1), 1977, may be obtained in accordance with the present invention, such as ascorbic, fumaric, methane sulfonic, citric, hippuric, tartaric hydrochloric and the like.

In preparing the maleic acid salt of the compounds of the present invention, the product containing the isomers in the ratio described above is dissolved in a solvent, such as ethyl acetate, acetonitrile, toluene diethyl ether or acetone, to which maleic acid in a 1 to 10, preferably in a 1 to 2 molar equivalent is added and the mixture agitated with or without heating to obtain a clear solution. The clear solution is then cooled to less than room temperature, preferably to 0° to 5° C. to obtain a precipitate, such as crystals, which is then collected, such as by suction filtration. The product so obtained is the desired (S,S) diastereoisomer, maleic acid salt.

The following examples will further illustrate the process of the present invention.

EXAMPLE 1

Preparation of N[(1S)-1-(Ethoxycarbonyl)-3-Phenylpropyl]-L-Alanine, t-Butyl Ester, Maleic Acid Salt (S,S)

To 50 ml of absolute ethanol was added t-butyl L-alanate (S) (5.0 g, 38.1 mmol) (obtained from Austin Chem. Co., a distributor of Anjimoto Chemical Co.) to form a basic solution (pH=8–9.0). The solution was adjusted to pH 4–5.0 by the addition of 10 ml of glacial acetic acid. To this solution was then added ethyl 2-oxo-4-phenylbutyrate (15.0 g, 72.7 mmol) (Austin Chemical Company), 13A° molecular sieves and 10% palladium on activated carbon (0.5 g). The resulting reaction mixture was then hydrogenated on a Parr hydrogenator at 40 PSI for 64 hours. The catalyst was removed by filtration through celite and the filtrate concentrated in vacuo to a thick oil. Analytical HPLC of this crude reaction mixture showed a 60/40 mixture of the N[(1S)-1-(ethoxycarbonyl)-3-phenylpropyl]-L-alanine, t-butyl ester(S,S)/N[(1R)-1-(ethoxycarbonyl)-3-phenylpropyl]-L-alanine, t-butyl ester (R,S).

The thick oil was then dissolved in 50 ml of hot toluene and maleic acid (2.5 g, 21.6 mmol) was added to form a clear solution. Upon cooling at 5° C., crystals formed which were collected by suction filtration. The dried product, N[1(S)-1-(ethoxycarbonyl)-3-phenylpropyl]-L-alanine, t-butyl ester, maleic acid salt (S,S) was obtained as a single diastereomer (S,S) in 52% theoretical yield. The product was characterized by NMR, IR, MS(CI) and had mp=110°–112°; [α]$_D$=+6.7°, [α]$_{365}$=+38.0° (C=1.0, MeOH). Anal. Calcd. for:

$C_{19}H_{29}NO_4 \cdot C_4H_4O_4 \cdot 3/2H_2O$: C, 57.73; H, 7.58; N, 2.93; Found: C, 57.34; H, 6.96; N, 3.07.

EXAMPLE 2

Preparation of N[(1S)-1-(Ethoxycarbonyl)-3-Phenylpropyl]-L-Phenylalanine, Methyl Ester, Hydrochloric Acid Salt (S,S)

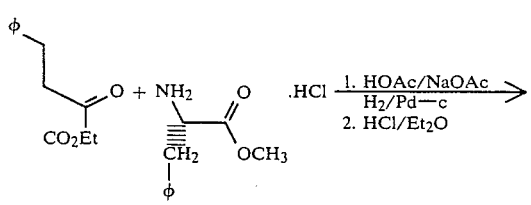

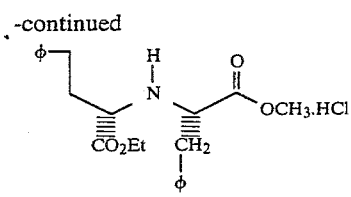

To 175 ml of methanol was added methyl L-phenylalanine (S) hydrochloric acid salt (9.0 g, 41.7 mmol) (obtained from Aldrich Chemical Company). The solution was adjusted to pH4–5.0 by the addition of 10 ml of glacial acetic acid and 6.0 g of anhydrous sodium acetate. To this reaction mixture was then added ethyl 2-oxo-4-phenylbutyrate (18.0 g, 86.9 mmol) (Austin Chemical Company) and 10% palladium on activated carbon (0.8g). The resulting reaction mixture was then hydrogenated on a Parr hydrogenator at 45–50 PSI for 62 hours. The catalyst was removed by filtration and the filtrate concentrated in vacuo to a thick oil. Analytical TLC showed only one major product, N[(1S)-1-(ethoxycarbonyl)-3-phenylpropyl]-L-phenylalanine, methyl ester (S,S).

The crude reaction mixture was then dissolved in diethyl ether and the solution saturated with anhydrous hydrogen chloride gas. The resulting solution was diluted with heptane to precipitate an oil. The supernatant was decanted and the oil triturated with two successive portions of fresh heptane to yield a white solid which was collected by suction filtration. The dried product, N[(1S)-1-(ethoxycarbonyl)-3-phenyl-propyl]-L-phenylalanine, methyl ester, hydrochloric acid salt (S,S) was obtained as a single diastereomer (S,S) in 68% theoretical yield. An analytical sample, recrystallized from ethyl acetate was characterized by NMR, IR and had mp=119°–123°; $[\alpha]_D = +27.9°$, $[\alpha]_{365} = +116.7°$(C=1.0, MeOH).

Anal. Calcd. for: $C_{22}H_{27}NO_4 \cdot HCl$. C, 65.09%; H, 6.95%; N, 3.45%; Found: C, 65.04%; H, 6.85%; N, 3.26%.

EXAMPLE

Preparation of N[1-(Ethoxycarbonyl)-3-Phenylpropyl]-L-Tryptophan, Methyl Ester, Hydrochloric Acid Salt (S,S & R,S)

Ten grams (0.04 mole) of L-tryptophan, methyl ester, hydrochloride salt (obtained from Sigma Chemical Company) were dissolved in 150 ml of methanol. Twenty grams of ethyl 2-oxo-4-phenylbutyrate were added and the pH was adjusted to 4–5 with 2.8 g of anhydrous sodium acetate. One gram of 10% palladium on activated carbon was then added and the resulting mixture was hydrogenated at about 50 psi pressure for 62 hours at room temperature. The catalyst was removed by filtration. The filtrate was diluted with 500 ml of water and extracted with 150 ml of methylene chloride. Methylene chloride extract was washed with water, dried with anhydrous magnesium sulfate and the solvent was evaporated on a rotary evaporator. The oily residue was dissolved in 250 ml of anhydrous diethyl ether. Dry hydrogen chloride gas was passed through the solution to precipitate the product as an off-white solid which after filtering and drying weighed 13.5 g (77%). NMR shows the product to be a mixture of S,S and R,S diastereomers in which the S,S isomers predominates by a ratio of 2:1. Elemental analysis: calculated for $C_{24}H_{28}N_2O_4 \cdot HCl$: C 64.78%; H 6.57%; N 6.29%. Found: C 64.74%; H 6.32%; N 6.38%.

The compounds of the present invention possess valuable pharmaceutical properties as intermediates for the preparation of Angiotensin Converting Enzyme Inhibitor (ACEI) compounds. The intermediates or products of their hydrolysis can be reacted with appropriately substituted amino compounds, using standard techniques and reaction conditions, to form compounds which are useful in treating hypertension. The resulting dipeptides are described in greater detail in Belgian Pat. No. 892,552 and No. 892,669. The compounds disclosed in these patents include stereoisomeric forms which can be resolved by a stereospecific route or resolution of mixtures of isomers. It was found that the compounds in which the S-configuration exists at all asymmetric centers are the most active; those in which the R-configuration exist are of less activity; and those where both R- and S- configurations exist are of intermediate activity.

The stereoselective process of the present invention utilizes readily available raw materials, it is simple, inexpensive and easily adaptable for large scale synthesis of the desired (S,S) intermediates that may be used in the preparation of the most active Angiotensin Converting Enzyme Inhibitor compounds disclosed in the above-referred to Belgian Pat. No. 892,552 and No. 892,669.

What is claimed is:

1. A process of preparing the compound of the formula

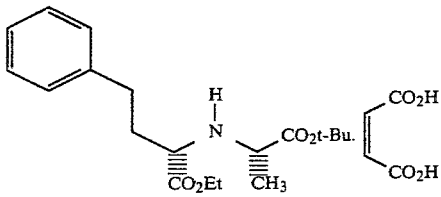

comprising the steps of:

a., dissolving the compound of the formula

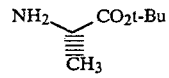

in a reaction medium to form a solution;
b., adjusting the pH of the solution to about 4.0 to 5.0;
c., adding with mixing the compound of the formula

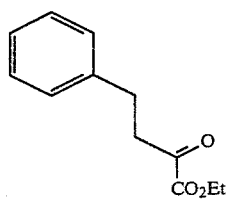

to the solution to form a mixture;
d., adding a hydrogenation catalyst to form a reaction mixture;
e., hydrogenating the reaction mixture;
f., removing the catalyst;
g., isolating a crude product;

h., reacting the crude product with maleic acid to form the desired compound.

2. The process of claim 1 wherein said reaction medium is selected from the group consisting of an alcohol, a polar solvent or a mixture of water and a water miscible solvent.

3. The process of claim 2 wherein said alcohol is selected from the group consisting of methyl, ethyl and propyl alcohol.

4. The process of claim 2 wherein said polar solvent is THF, dioxane, ethyl acetate, diethylether and acetonitrile.

5. The process of claim 1 wherein said hydrogenation catalyst is selected from the group consisting of palladium, platinum and nickel.

6. The process of claim 1 wherein said hydrogenation catalyst is present in an amount of 0.1 to 20% w/w based on the weight of the reagents.

7. The process of claim 1 wherein said hydrogenation catalyst is present in a catalyst support selected from the group consisting of carbon, silica and zeolite.

8. The process of claim 1 wherein said hydrogenation is performed at a temperature of 0° to 100° C.

9. The process of claim 1 wherein said isolating step is by partitioning a filtrate between a water miscible solvent and water to form an organic solvent extract containing the dissolved product.

10. The process of claim 9 wherein said water immiscible solvent is selected from the group consisting of toluene, ethyl acetate, chloroform and methylene chloride.

11. The process of claim 1 wherein said isolating step is by precipitating the crude product and removing the solvent therefrom.

12. The process of claim 11 wherein removing said solvent is by filtration.

13. The process of claim 1 wherein the reacting of the crude product with maleic acid is performed in a solvent medium.

14. The process of claim 13 wherein said solvent medium is selected from the group consisting of ethyl acetate, acetonitrile, toluene, diethylether and acetone.

15. The process of claim 1 wherein the desired maleic acid salt is precipitated from said solvent medium by cooling to about 5° C.

16. The process of claim 15 further comprising removing said maleic acid salt precipitate from said solvent medium.

* * * * *